(12) United States Patent
Dooley et al.

(10) Patent No.: US 7,794,606 B2
(45) Date of Patent: Sep. 14, 2010

(54) MODULAR FLAMELESS WASTE TREATMENT METHOD

(75) Inventors: Joseph B. Dooley, Kingston, TN (US); Jeffrey G. Hubrig, Knoxville, TN (US); Richard A. Lowden, Clinton, TN (US)

(73) Assignee: Innovation Services, Inc., Knoxville, TN (US)

( * ) Notice: Subject to any disclaimer, the term of this patent is extended or adjusted under 35 U.S.C. 154(b) by 652 days.

(21) Appl. No.: 11/697,921

(22) Filed: Apr. 9, 2007

(65) Prior Publication Data

US 2008/0245748 A1    Oct. 9, 2008

(51) Int. Cl.
*C02F 1/50* (2006.01)
*C02F 1/72* (2006.01)

(52) U.S. Cl. ............... 210/752; 205/756; 210/748.17; 210/762; 210/764; 210/765

(58) Field of Classification Search .............. 210/764
See application file for complete search history.

(56) References Cited

U.S. PATENT DOCUMENTS

| | | | | |
|---|---|---|---|---|
| 3,703,453 | A * | 11/1972 | Gordy et al. ............... | 588/303 |
| 3,925,176 | A * | 12/1975 | Okert ....................... | 205/701 |
| 4,054,139 | A | 10/1977 | Crossley | |
| 4,174,280 | A | 11/1979 | Pradt et al. | |
| 4,179,347 | A * | 12/1979 | Krause et al. .............. | 205/743 |
| 4,292,175 | A * | 9/1981 | Krause et al. .............. | 210/192 |
| 5,073,298 | A * | 12/1991 | Gentle et al. .............. | 516/117 |
| 5,073,382 | A | 12/1991 | Antelman | |
| 5,077,007 | A * | 12/1991 | Pearson .................... | 422/3 |
| 5,078,902 | A | 1/1992 | Antelman | |
| 5,248,486 | A | 9/1993 | Matsuoka et al. | |
| 5,531,865 | A | 7/1996 | Cole | |
| 5,820,541 | A * | 10/1998 | Berlanga Barrera ....... | 588/249.5 |
| 5,820,761 | A | 10/1998 | Holzer et al. | |
| 5,919,367 | A | 7/1999 | Khudenko | |
| 6,096,219 | A * | 8/2000 | Green et al. ............... | 210/695 |
| 6,126,830 | A * | 10/2000 | Marshall ................... | 210/627 |
| 6,746,593 | B2 * | 6/2004 | Herbst ...................... | 205/757 |
| 6,783,679 | B1 | 8/2004 | Rozich | |
| 7,387,719 | B2 * | 6/2008 | Carson et al. ............. | 205/688 |
| 7,691,251 | B2 * | 4/2010 | Carson et al. ............. | 205/688 |

(Continued)

FOREIGN PATENT DOCUMENTS

WO    2006065825    6/2006

OTHER PUBLICATIONS

H.T. Michels et al., Copper Alloys for Human Infectious Disease Control, Materials Science and Technology Conference, Sep. 25-28, 2005, Pittsburg, PA.

(Continued)

*Primary Examiner*—Peter A Hruskoci
(74) *Attorney, Agent, or Firm*—Luedeka, Neely & Graham, P.C.

(57) ABSTRACT

A modular waste treatment system for substantially liquid waste streams and methods of treating liquid waste streams are disclosed. The modular waste treatment system includes a maceration chamber for initial treatment and homogenization of waste material; a metal ion infusion chamber in fluid flow communication with the maceration chamber for introducing metal ions into the waste material; and an oxidation chamber for wet oxidation of the waste stream.

8 Claims, 4 Drawing Sheets

U.S. PATENT DOCUMENTS

2005/0199557 A1     9/2005    Johnston et al.
2006/0175266 A1     8/2006    Rima et al.

OTHER PUBLICATIONS

William H. Dresher, Copper Helps Control Deadly Prion Protein Infection, Innovations in Copper, Oct. 2006, 1-4.

Silver, Nature's Water Purifier, www.doulton.ca/silver.html., Feb. 27, 1997, 1-6.

Tests Show Silver Best "Swimming Pool" Water Purifier, The Silver Institute Letter, May 1975, vol. VI, No. 11.

Dual Sanitation with Copper Silver Ion, Ideal Distributors Limited, 2007, 1-4.

Leonard Zimmerman, Toxicity of Copper and Ascorbic Acid to Serratia Marcescens, Journal of Bacteriology, Apr. 1966, 1537-1542, vol. 91, No. 4.

F. X. Abad et al., Disinfection of Human Enteric Viruses in Water by Copper and Silver in Combination with Low Levels of Chlorine, Applied and Environmental Microbiology, Jul. 1994, 2377-2383, vol. 60, No. 7.

M.T. Yahya et al., Disinfection of Bacteria in Water Systems by Using Electrolytically Generated Copper: Silver & Reduced Levels of Free Chlorine, Canadian Journal of Microbiology, 1990, 109-116, vol. 36.

J. A. Spardo et al., Antibacterial Effects of Silver Electrodes with Weak Direct Current, Antimicrobial Agents and Chemotherapy, Nov. 1974, 637-642, vol. 6, No. 5.

Andrew A. Marino, Electrochemical Properties of Silver-Nylon Fabrics, Journal of the Electrochemical Society, Electrochemical Science and Technology, Jan. 1985, 68-72, vol. 132, No. 1.

H. Akiyama, Prophylaxis of Indwelling Urethral Catheter Infection: Clinical Experience with A Modified Foley Catheter And Drainage System, The Journal of Urology, 1979, 40-42, vol. 121.

C. P. Davis, Iontophoretic Killing of *Escherichia coli* in Static Fluid and in a Model Catheter System, Journal of clinical Microbiology, May 1982, 891-894, vol. 15, No. 5.

Oligodynamic Ag: The Active Ingredient in Sovereign Silver and Argentyn 23, Natural-Immunogenics Corp.

Q. L. Feng et al., A Mechanistic Study of the Antibacterial Effect of Silver Ions on *Escherichia coli* and *Staphylococcus aureus*, Journal of Biomedical Materials, 2000, 662-668, vol. 52.

J. O. Noyce et al., Use of Copper Cast Alloys to Control *Escherichia coli* O157 Cross-Contamination During Food Processing, Applied and Environmental Microbiology, Jun. 2006, 4239-4244, vol. 72, No. 6.

John Apsley et al., Nanotechnology's Latest Oncolytic Agent: Silver, Cancer, & Infection Associations, Townsend Letter for Doctors and Patients, May 2006.

Charles F. McKhann, M.D. et al., Oligodynamic Action of Metallic Elements and of Metal Alloys on Certain Bacteria and Viruses, Dec. 1985, 95-101, vol. 182(1).

Studies and Published Papers on Ionisation, Copper, Chlorine Efficacy and Related Issues, http:/www.ecosmarte.com.au, Mar. 13, 2007, 1-95.

I.B. Romans, Oligodynamic Metals, Disinfection, Sterilization, and Preservation, 1968, Chapter 24, 372-400, Lea & Febiger, Philadelphia.

I.B. Romans, Silver Compounds, Disinfection, Sterilization, and Preservation, 1968, Chapter 28, 469-474, Lea & Febiger, Philadelphia.

\* cited by examiner

MODULAR FLAMELESS WASTE TREATMENT METHOD

TECHNICAL FIELD

The disclosure relates to modular treatment unit intended to provide for treatment and/or disinfection of liquid wastes, including medical, domestic, scientific, mortuary, or commercial wastes, to disinfect and render the wastes non-infectious and less toxic.

BACKGROUND AND SUMMARY

There is growing concern that waste streams from hospitals, slaughter houses, and other sources that may contain biologically hazardous and other toxic or objectionable components are not adequately treated before discharging such waste streams to sanitary sewer systems or directly to the environment. Large municipal treatment facilities may not adequately be configured for high concentrations of biological and chemical materials originating in hospitals and other sources. Accordingly, there is a need for improved systems and methods for treating waste streams before the streams are discharged into a sanitary sewer system or directly to the environment. There is also a need for modular systems that may be readily deployed before an inlet to an existing sanitary sewer system at the source of the waste stream thereby reducing the infectivity and toxicity of material that a municipal system must treat.

In view of the foregoing and other needs, an exemplary embodiment of the disclosure provides a modular waste treatment system for liquid waste streams and methods of treating liquid waste streams are disclosed. The modular waste treatment system includes a maceration chamber for initial treatment and homogenization of waste material; a metal ion infusion chamber in fluid flow communication with the maceration chamber for introducing metal ions into the waste material; and an oxidation chamber for wet oxidation of the waste stream. Provision may be made to recycle the waste to one or more of the chambers for further treatment if required.

Another exemplary embodiment of the disclosure provides a method of treating a liquid waste material to provide a treated waste stream. The method may include flowing a waste stream into a modular waste treatment system. The modular waste treatment system may include a maceration chamber for initial treatment and homogenization of waste material; a metal ion infusion chamber in fluid flow communication with the maceration chamber for introducing metal ions into the waste material; and an oxidation chamber for oxidizing oxidizable material in the waste stream. The waste stream is macerated to a predetermined particle size and may be contacted with a film inhibitor in the maceration chamber. Metal ions are generated in the metal ion infusion chamber for contact with the waste stream from the maceration chamber to partially detoxify and to promote the oxidation process of the waste stream. The waste stream is then oxidized in the presence of oxygen to provide a treated stream that is substantially devoid of toxic and active biological materials.

An advantage of the system and methods described herein is that the system combines at least two disinfection techniques in a single unit thereby increasing the effectiveness of waste stream treatment over the use of a single disinfection technique. The oxidation system used is essentially flameless and therefore does not introduce any combustion products into the atmosphere. However, heating both the waste stream and the oxygen stream may greatly promote the reaction rate. The use of elemental oxygen also provides a much more compact system than units using air (containing only about 20 wt. % oxygen).

Because of the modular components of the system, the system may be configured as a mobile, or portable, stand-alone unit or may be provided in a substantially fixed non-portable installation that may be inserted between a waste material source and a final disposition of the waste material. The waste treatment system may also be combined and/or integral with a waste collection system. In another embodiment, the waste treatment system may be a stand alone system for discharge of treated wastes to the environment.

Additional objects and advantages of the disclosure will be set forth in part in the description which follows, and/or can be learned by practice of the disclosure. The objects and advantages of the disclosure may be realized and attained by means of the elements and combinations particularly pointed out in the appended claims.

It is to be understood that both the foregoing general description and the following detailed description are exemplary and explanatory only and are not restrictive of the disclosure, as claimed.

BRIEF DESCRIPTION OF THE DRAWINGS

Further advantages of the exemplary embodiments may become apparent by reference to the detailed description of the exemplary embodiments when considered in conjunction with the following drawings illustrating one or more non-limiting aspects thereof, wherein like reference characters designate like or similar elements throughout the several drawings as follows.

DESCRIPTION OF THE EXEMPLARY EMBODIMENTS

As described in more detail below, embodiments of the disclosure provide systems and methods for treating waste streams before discharging the waste streams to a sanitary sewer system or directly to the environment. The systems and methods may be adaptable to being portable or being attached to existing sanitary sewer drains for multiple locations. Each system may be substantially self-contained so that fluid discharged from the system may be suitable to flow into an existing sanitary sewer without further treatment or for flow directly to the environment without further treatment.

The systems and methods of the present disclosure may generate reactive disinfection agents in situ during the course of operation of the system. Waste streams may be treated with a synergistic combination of metal ions and a wet oxidation step. Because the metal ions are effective at low concentrations and because they are rendered inert during oxidation; no further treatment to remove the metal ions is required. An oxygen demand sensor may be included to ensure the effectiveness of treatment before discharge of the treated stream to a sewer system or the environment.

While metal ions used in combination with oxidizing agents such as chlorine are known to be effective biocidal agents, the combination of metal ions and a wet oxidation step in a single system may provide a synergistically improved effectiveness for eliminating biological activity and reducing the toxic effect of components in the waste stream.

Figure 1:
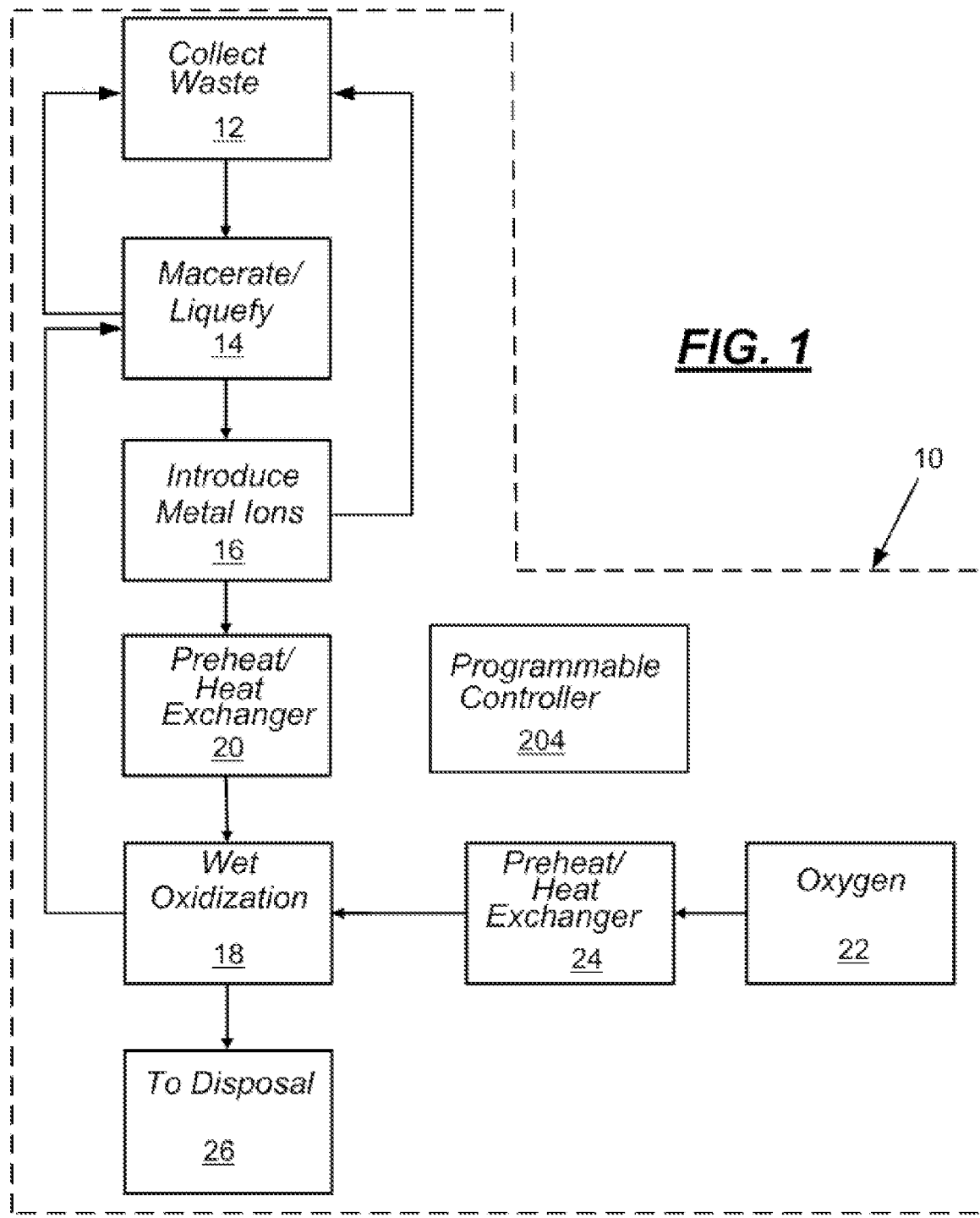
FIG. 1 is a block flow diagram of a treatment process according to the disclosure.

With reference to FIG. 1, an embodiment of the disclosure provides a waste treatment unit 10 for performing a series of continuous, in-line processes, with each process stage described in more detail below. Each process stage may herein be represented as an individual physical chamber in order to provide clear understanding of the in-line process concept.

As illustrated schematically in FIG. 1, an overview of the treatment system 10 is presented. The treatment system 10 includes a waste collection step 12 for collecting waste liquid to be treated. After collection, the waste liquid is macerated in a maceration step 14 in order to reduce the size of solid particles and homogenize the particles and waste in the waste stream to a size that can be effectively treated with metal ions and wet oxidation in later stages of the process. As shown, the macerated liquid may be recycled to mix with the waste liquid being collected in step 12 to promote mixing and homogenization and to extend the time of contact with the active chemicals. Water or other aqueous solution may be added to the waste collected in step 12 to promote flow through the system 10.

Next, a metal ion infusion step 16 is provided to generate or otherwise infuse metal ions into the waste liquid for metal ion treatment of the waste liquid and to promote the oxidation process. The macerated liquid may be recirculated through the metal ion infusion stage in multiple passes to ensure adequate concentrations of metal ions.

The metal ion treated liquid is then oxidized in a wet oxidation step 18. The wet oxidation step may be enhanced by heating the metal ion treated liquid in a preheat step 20 prior to the wet oxidation step 18. The wet oxidation step 18 is conducted using oxygen gas 22, in conjunction with the metal ions to effect a low temperature chemical reaction. According to embodiments of the disclosure, pure oxygen is the most desirable oxygen gas for conducting the oxidation step of the process 10 because it substantially reduces the volume requirements for treating the waste. Based upon the readings from an oxygen demand sensor, the waste may be recycled or may be suitable for disposal according to step 26 of the process 10.

Figure 2:
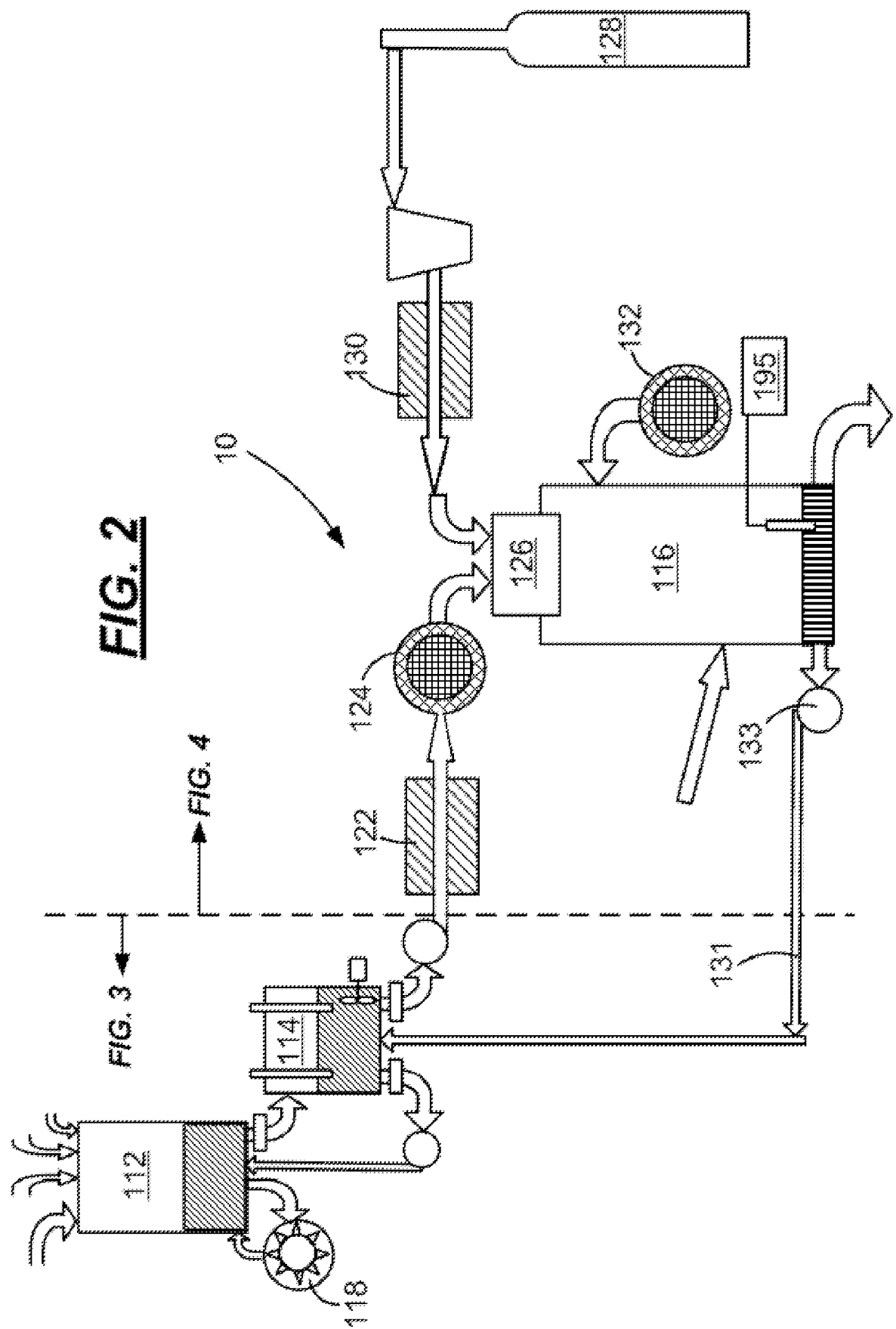
FIG. 2 is an overall schematic drawing of a treatment system according to the disclosure.

As shown in FIG. 2, the main components of the system 10 include a receiving chamber 112, a metal ion infusion chamber 114, and an oxidation chamber 116. A macerator 118 may be associated with the receiving chamber 112 or may be associated with the metal ion infusion chamber 114 or both. Additional process chemicals such as an anti-foam and a film inhibitor may be provided to the waste liquid in the receiving chamber 112. A heat exchanger or other heating means 122 is provided to preheat the metal ion treated liquid prior to introducing the treated liquid into the oxidation chamber. The metal ion treated liquid is also pressurized with a pressure pump 124 for feeding into a spray mixing nozzle 126 for feed, along with an oxidizing agent, into the oxidation chamber 116. An oxygen source 128 is provided for feeding oxygen gas to the oxidation chamber 116. The oxygen gas may also be preheated in a heat exchanger or by other heating means 130. The oxidation chamber 116 may also be pressurized by a compressor or pressure pump 132 associated with the chamber 116. A portion of the metal ion treated and oxidized material in the oxidation chamber 116 may be recirculated through recirculation line 131 by recirculation pump 133 to the metal ion infusion chamber 114. Further details of the components of the system 10 are provided in FIGS. 3 and 4 discussed below.

Receiving Chamber

Figure 3:
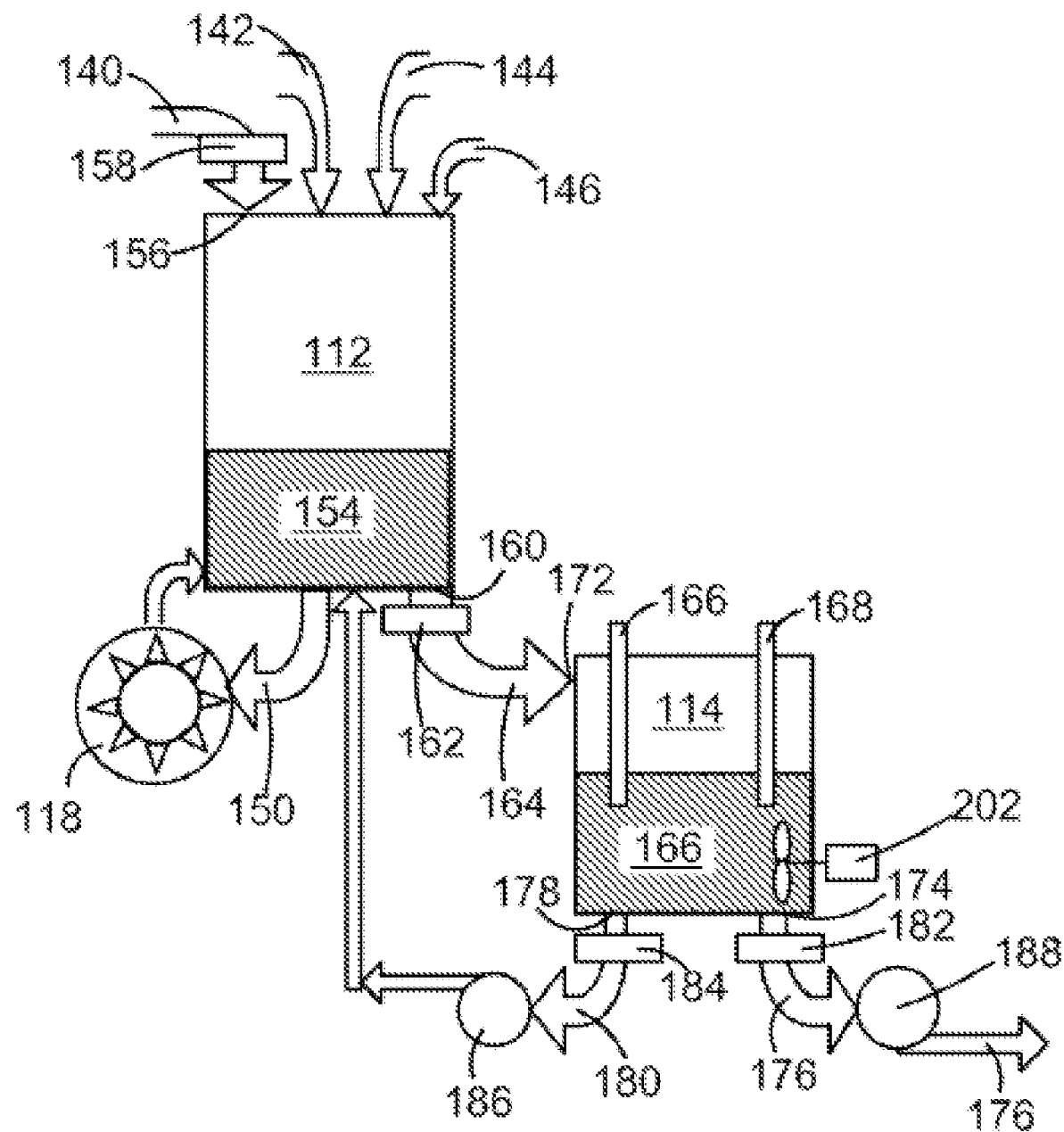
FIG. 3 is an enlarged schematic drawing of a portion of the treatment system of FIG. 2 including a receiving chamber and a metal ion infusion chamber.

As shown in FIG. 3, a waste stream 140 comprising biological waste may be fed into the receiving chamber 112 where it may be mechanically macerated in the macerator 118 and combined with tap water 142 or other aqueous fluids such as a saline solution to provide a pumpable slurry. Depending on the biological or lipid content of the waste stream, a metered dose of a lipid/protein complex film inhibitor 144 may be provided to the receiving chamber 112. A suitable film inhibitor 144 may be an aqueous solution of sodium lauryl sulfate (SLS). Optionally, a foam suppressant 146, such as an organosilicone compound, may also be added to the receiving chamber 112 to reduce foaming tendencies of the waste stream 140. In an alternative embodiment, metal ions from a metal ion solution may be metered into the receiving chamber using a dosing pump. The receiving chamber 112 may be constructed of copper or copper alloy to provide an inherent bactericidal action thereby suppressing undesirable bacterial growth. Similar bactericidal action may be obtained by copper plating or use of a copper or copper alloy floor plate in the receiving chamber 112.

The film inhibitor 144 is believed to perform two critical functions. First, the film inhibitor 144 may initiate a chemical attack to begin breaking down and denaturing both lipid and protein complexes present in the waste material 154. Second, the film inhibitor's inherent detergency may enable the receiving chamber 112 to remain "self-cleaning". An amount of film inhibitor 144 that may be used in the receiving chamber 112 may range from about 0.1 to about 10 percent by volume.

The foam suppressant 146 may further ensure that air bubble formation in the waste material 154 is reduced during maceration cycles, so that air entrapment does not inhibit the operating efficacy of subsequent treatment chambers. An amount of foam suppressant 146 that may be used in the receiving chamber 112 to suppress air bubble formation may range from about 0.05 to about 1.0 percent by volume.

The receiving chamber 112 may include a macerating device 118, such as a pump, a rotary paddle or blade, or other means of chopping or mixing the recirculated stream 150 from the chamber 112 in order to macerate and mix the incoming waste stream 140 with the water 142, film inhibitor 144 and/or foam suppressant 146. Maceration may effectively break down waste solids in the waste material 154 to a common rough particle size and to suitably mix waste solids in the waste material 154 with sufficient fluid for flow to subsequent chambers for waste processing. Multiple maceration steps may be used to provide a suitable particle size in the waste material 154 for subsequent treatment.

Accordingly, the waste material 154 is macerated to provide a substantially liquid stream. The term "substantially liquid" means that any solids present in the waste material remain substantially suspended in a liquid phase for flow through the system 10.

A suitable particle size exiting the receiving chamber 112 may be less than about 0.5 millimeters in diameter and typically less than .3 millimeters in diameter after maceration. For example, the maximum particle size exiting from the macerating device 118 may range from about 0.25 to about 0.5 millimeters in diameter. The initial particle size of particles entering the macerating device 118 may range from about 5 to about 10 millimeters in diameter. The term "diameter" is used to signify an average cross-sectional dimension of particles based on the largest cross-section of the particles in the waste material 154 and is not intended to indicate that the particles are necessarily circular or spherical.

The chamber 112 may further include a fluid inlet port 156 that may include a unidirectional inlet valve 158 or pump unit for allowing the waste stream 140 to enter the chamber 112. The chamber 112 may have a fluid exit port 160 containing a unidirectional exit valve 162 or pump unit for allowing the waste stream 164 as a slurry or suspension of solids to exit the chamber 112. The inlet and exit ports 156 and 160 may be positioned on opposite sides of the receiving chamber 112, or they may be otherwise configured to provide flow into and out of the chamber 112 as required to maintain a predetermined level of liquid in the chamber 112. In that regard a suitable level control device may be used to maintain a predetermined level of fluid in the chamber 112.

Metal Ion Infusion Chamber

The waste stream 164 may then flow from the receiving chamber 112 into the metal ion infusion chamber 114 where a set of electrodes comprising an anode 166 and a cathode 168, each composed of one or more metals selected from silver, copper, iron, zinc, bismuth, gold, aluminum and/or other metals may be immersed in the waste material suspension 166. Although iron is an effective metal species for promoting oxidation; other metal ions may be suitable for this application. Application of electrical energy to the anode 166 and the cathode 168 may cause metal ions to be liberated from the electrodes via one or more redox reactions, whereby the metal ions may become dissolved in the waste material suspension 166. The voltage and current applied to the electrodes may be externally regulated in order to exercise control over the concentration of metal ions that may be dissolved in the waste suspension 166.

Multiple sets of electrodes comprising one or more metal compositions, and having an appropriate voltage division and current flow may introduce various concentrations of one or more metal ions into the waste suspension 166.

The dissolved metal ions may act within the waste suspension 166 to deactivate or destroy bacterial, protist, fungal, and viral infectious agents present within the waste suspension 166. The deactivation or destruction of infectious agents according to embodiments of the disclosure may be herein referred to as "disinfection." Particularly suitable metal ions for use as disinfection agents include copper and silver ions. It is believed that a concentration of copper ions that is much greater than a concentration of silver ions is particularly suitable for disinfection of waste liquids. Although, a concentration ratio of 10:1 Cu to Ag has been found to be highly effective; other ratios may prove to be suitable for this application. Accordingly, ions of different metals may be produced at different concentration levels in order to provide a suitable total dissolved metal ion concentration. In one embodiment, a suitable copper ion concentration may range from about 100 ppm to about 1000 ppm, with a further suitable example being about 400 ppm of copper ions. Likewise, suitable silver ion concentration may range from about 10 ppm to about 100 ppm, with a further suitable example being about 40 ppm of silver ions. A suitable total metal ion concentration for disinfection may range from about 110 ppm to about 1100 ppm. As a further example, a suitable total metal ion concentration may range from about 200 ppm to about 800 ppm, and as another suitable example a total metal ion concentration may range from about 300 ppm to about 600 ppm.

Accordingly, ions of different metals may be produced at different concentration levels in order to provide a suitable total dissolved metal ion concentration. A metal ion exposure time ranging from about 60 seconds to about 30 minutes may be suitable to provide disinfection to the waste stream.

The electrodes used to produce the metal ions may be pure metals in which case multiple electrodes are used and voltages and currents to each electrode are regulated in order to control the various metal ion concentrations. The electrodes may also be composed of a mixture of more than one metal, such as a metal alloy, in order to control the concentration of each ion in solution. For example, a process for producing a higher concentration of copper ions and a lower concentration of silver ions may use electrodes containing substantially more copper than silver.

In a further embodiment, the electrodes may be fabricated employing powder metallurgy. A further embodiment using copper powder and silver or silver-alloy "solder" may be employed as a binder. The powdered metal electrodes may be fabricated such that the concentration of exposed metals such as copper or silver is controlled to produce the desired concentration ratio of metal ions. Additionally, the composition of an electrode and its corresponding ionic contribution may be controlled through particle size and amount of each phase, primary metal and "binder" present in the powder molded electrode. For example, large spherical grains of copper may be pressed with silver solder powder and sintered to form an electrode with higher surface concentrations of copper.

In a further embodiment of the disclosure, the electrodes may be integrated into a mixing pump in which the vanes or other metal portions of the pump may act as electrodes.

The metal ion infusion chamber 114 may also be equipped with an inlet port 172 for flow of fluid from the receiving chamber 112 into the metal ion infusion chamber 114, and a first exit port 174 for flow of ion treated material 176 out of the metal ion infusion chamber 114. A second exit port 178 may be provided for the metal ion infusion chamber 114 for recirculation of a portion 180 of the waste material suspension 166 back into the waste stream 164 entering the meal ion infusion chamber 114. The exits ports 174 and 178 may include directionally restrictive fluid flow valves 182 and 184 that provide unidirectional fluid flow through the valves 182 and 184. A recirculation pump 186 may be included to circulate the portion 180 of the metal ion waste material suspension 166 back into the metal ion infusion chamber 114.

Oxidation Chamber

Figure 4:
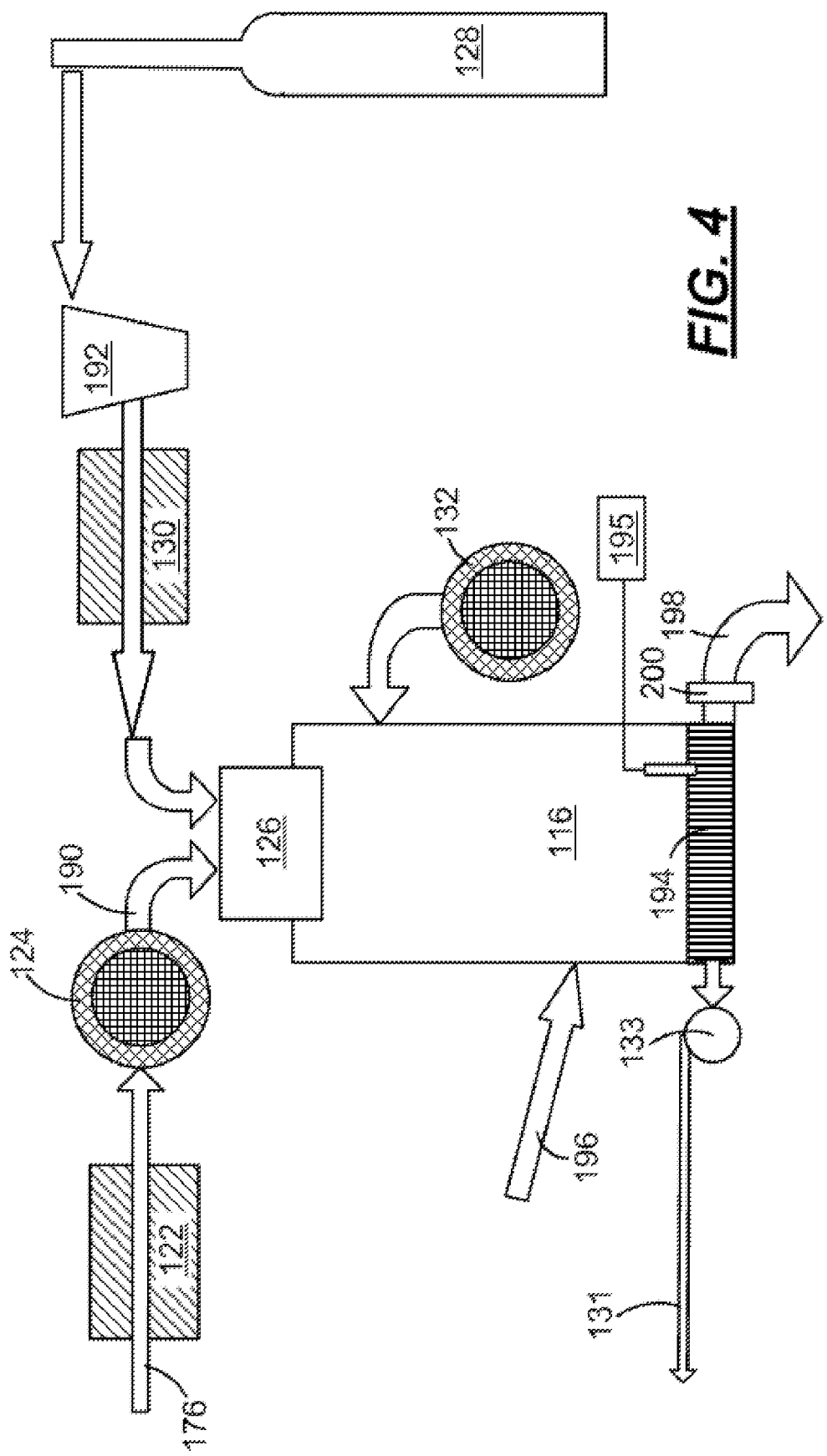
FIG. 4 is an enlarged schematic drawing of a portion of the treatment system of FIG. 2 including an oxidation chamber.

As shown in FIG. 4, the metal ion treated material 176 may then flow into the oxidation chamber 116 for wet oxidation of the waste material. A pump 188 (FIG. 3) may be used to pump the metal ion treated material 176 through the heat exchanger or other heating means 122 and through the pressurizing pump 124 to provide a pressurized waste material 190 into the spray mixing nozzle 126 and into the chamber 116. The metal ion treated material 176 is typically preheated to a temperature ranging from about 100° C. to about 200° C. prior to introducing the material 176 to the oxidation chamber 116.

The oxygen supply 128 provides pure oxygen, or an oxygen containing gas, such as air, through a pressure regulating valve 192 and the oxygen heat exchanger or other heating means 130 into the spray mixing nozzle 126 for intimate mixing with a relatively fine mist of the material 190. The heat exchanger or other heating means 130 may be used to heat the oxygen to a temperature ranging from about 100° C. to about 350° C. before mixing the heated oxygen with the pressurized waste material 190. The oxidation chamber may be further pressurized by the compressor 132 to provide a chamber operating pressure in the range of from about 0.01 to about 0.2 MPa above ambient pressure. Removal of metal ions from the pressurized waste material 190 prior to flow of the waste material 190 into the oxidation chamber 116 is not necessary as the metal ions may further aid in the oxidation treatment step of the process.

In the oxidation chamber 116, the chemical oxygen demand (COD) and/or biological oxygen demand (BOD) of oxidized liquid 194 formed in the oxidation chamber 116 may be monitored with sensors, such as an oxygen demand sensor 195 (FIG. 4), to determine the amount of oxygen required to treat all of the incoming waste material 190. A target resulting COD or BOD for the treated waste material 88 is in a range defined by regulatory requirements at a user's location.

According to the disclosure, oxidation of the pressurized waste 190 takes place in an aqueous environment wherein water is an integral part of the reaction. Water provides a medium for dissolved oxygen to react with organics and other oxidizable materials in the waste 190. It is believed that wet oxidation involves free radical formation with oxygen derived radicals attacking the organic compounds and resulting in the formation of organic radicals.

A noteworthy characteristic of wet oxidation chemistry is the formation of carboxylic acids in addition to $CO_2$ and water. Other oxidation products as a result of treating the waste material 190 in the oxidation chamber, may include, but are not limited to sulfur dioxide, nitrogen dioxide, and phosphorus pentoxide which may be dissolved in the oxidized liquid 194. The yield of carboxylic acids varies greatly depending on the design of the system and may formed with about 5 to about 10 weight percent of the total organic carbon (TOC) in the waste 190. The primary carboxylic acids formed as a result of wet oxidation include acetic acid, formic acid, and oxalic acid. Such carboxylic acids are typically biodegradable and conventional biological post treatment of the oxidized liquid 194 may be conducted to reduce the amount of acids in the liquid 194.

Additional water 196 or other aqueous fluid such as a saline solution may be added to the oxidized liquid 194 in order to provide a flowable waste exit stream 198. A flow control valve 200 may be included on the exit stream 198 to maintain a suitable liquid level in the oxidation chamber 116.

The system 10 may also include a programmable microcontroller 204 capable of interfacing with automatic controllers, temperature sensors, oxygen sensors, level sensors, conductivity sensors, pH sensors, and COD and/or BOD sensors to coordinate the activities of valves, pumps, heat exchangers or other heating means, pressure regulators, and macerators, to estimate the amount of waste being processed, and to control the electrode voltage and currents responsible for producing the metal ion disinfecting agents. An ability to reverse the polarity of the electrodes may be desirable to prevent and remove a build-up of residual mineral scale on the electrodes which may impede ion generation. Additional treatment chambers may be included with the system 10 to further treat the waste stream 140 and/or 198 before discharge to a sewer system or to the environment.

The system 10 may be particularly adapted to treating waste liquid streams 140 containing consumer and industrial waste materials. Such materials may include, but are not limited to, dairy shed waste, fowl waste, milk processing plant waste, food processing wastes, waste from the wine and brewery industries, food waste, shipboard waste, petroleum wastes, wool-scouring waste, sewage, medical waste, waster paper and paper products, paper production waste, rubber waste, saw dust and wood processing waste, plastic waste, and the like. Particularly suitable waste materials include those containing bacteria, surgical waste, biological or biologically toxic materials, pharmaceutical and personal care products.

In another alternative, a macerator or mixer 202 (FIG. 3) may be included in the metal ion infusion chamber 114 for further reducing the size of any solids present in the waste material suspension 166 or for providing intimate contact between the metal ions and the waste material suspension 166.

As used throughout the specification and claims, "a" and/or "an" may refer to one or more than one. Unless otherwise indicated, all numbers expressing quantities of ingredients, properties such as molecular weight, percent, ratio, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Other embodiments of the present disclosure will be apparent to those skilled in the art from consideration of the specification and practice of the embodiments disclosed herein. Accordingly, the embodiments are not intended to be limited to the specific exemplifications set forth hereinabove. Rather, the foregoing embodiments are within the spirit and scope of the appended claims, including the equivalents thereof available as a matter of law.

The patentees do not intend to dedicate any disclosed embodiments to the public, and to the extent any disclosed modifications or alterations may not literally fall within the scope of the claims, they are considered to be part hereof under the doctrine of equivalents.

What is claimed is:

1. A method of treating a liquid biological waste stream containing solid particles, and active biological or toxic waste components to provide a treated waste stream comprising the steps of:

flowing said waste stream containing solid particles into a waste treatment apparatus;

macerating the waste stream to reduce a size of the solid particles in the waste stream;

exposing the macerated waste stream containing solid particles to metal ions to disinfect the waste stream and to promote oxidation, wherein the metal ions comprise ions selected from the group consisting of aluminum, zinc, silver, iron, and copper ions;

preheating the metal ion exposed waste stream; and oxidizing the waste stream in the presence of the metal ions by exposing the waste stream to an oxygen-containing gas at a temperature effective for wet oxidation of the waste stream to provide a treated stream that is substantially devoid of toxic and active biological materials.

2. The method of claim 1, further comprising contacting the waste stream in the waste treatment apparatus with a foam inhibitor.

3. The method of claim 2, wherein the foam inhibitor comprises organosilicone compound.

4. The method of claim 1, wherein the step of oxidizing the waste stream comprises contacting the waste stream with pure oxygen.

5. The method of claim 1, further comprising recirculating the treated waste stream to the waste treatment apparatus.

6. The method of claim 1, further comprising heating the oxygen gas to a temperature ranging from about 100° to about 350° C. for the step of oxidizing the waste stream.

7. The method of claim 1, wherein the waste material to be treated is a waste material from a hospital containing biological and chemical materials.

8. The method of claim 1, wherein the metal ion exposed waste material is preheated to a temperature ranging from about 100° to about 200° C. prior to the step of oxidizing the waste stream.

\* \* \* \* \*